United States Patent [19]
Lee et al.

[11] Patent Number: 5,837,494
[45] Date of Patent: Nov. 17, 1998

[54] E. COLI MUTANT WITH SUPPRESSED ORGANIC ACID PRODUCTION

[75] Inventors: Jong Ho Lee; Han Choi; Il Lae Jung; Doe Sun Na; Young Min Park, all of Seoul, Rep. of Korea

[73] Assignee: Korea Green Cross Corporation, Kyungki-Do, Rep. of Korea

[21] Appl. No.: 860,529

[22] PCT Filed: Oct. 29, 1996

[86] PCT No.: PCT/KR96/00186

§ 371 Date: Jun. 30, 1997

§ 102(e) Date: Jun. 30, 1997

[87] PCT Pub. No.: WO97/16530

PCT Pub. Date: May 9, 1997

[30] Foreign Application Priority Data

Oct. 30, 1995 [KR] Rep. of Korea ........... 1995-38044

[51] Int. Cl.$^6$ .......................... C12P 21/06; C12N 15/00; C12N 1/20
[52] U.S. Cl. .............. 435/69.1; 435/172.1; 435/252.33; 435/252.8; 435/849; 935/73
[58] Field of Search ............... 435/69.1, 172.1, 435/252.33, 252.8, 849; 935/73

[56] References Cited

U.S. PATENT DOCUMENTS 5,028,539  7/1991  Ingram et al. .................. 435/161

FOREIGN PATENT DOCUMENTS 0 411 501  6/1991  European Pat. Off. .

OTHER PUBLICATIONS

Akihiko Mori, et al., Kinetic Studies on Submerged Acetic Acid Fermentation (IV) Product Inhibition and Transient Adaption of Cells to the Product, *J. Ferment. Technol.*, vol. 50, pp. 518–527, 1972.

Chih–Hsiung Chou, et al., "Effect of Modified Glucose Uptake Using Genetic Engineering Techniques on High–Level Recombinant Protein Production in *E. coli* Dense Cultures", *Biotech and Bioeng.*, vol. 44 pp. 952–960, 1994.

E. Bech Jensen, et al., "Production of Recombinant Human Growth Hormone in *E. coli*: Expression of Different Precursors and Physiological Effects of Glucose, Acetate, and Salts", *Biotech & Bioeng.*, vol. 36 pp. 1–11, 1990.

R.A. Majewski, et al., "Simple Constrained–Optimization View of Acetate Overflow in *E. coli*", *Biotechnology and Bioengineering*, vol. 35, pp. 732–738, 1990.

Jeffrey H. Miller, "A Short Course in Bacterial Genetics: A Laboratory Manual and Handbook for *E. coli* and Related Bacteria", pp. 215–267, 1992.

Kyung Tai Min, et al., "*Nucleic Acids Research*", vol. 16 pp. 5075–5088, 1988.

Kwahng–Rae Huh, et al., "Cloning and Expression of Human Lipocortin–1 cDNA in *E. coli*", *Korean Biochem J.* vol. 23, pp. 459–464, 1990.

Egon Amann, et al., 'ATG vectors' for regulated high–level expression of cloned genes in *E. coli, Gene* vol. 40 pp. 183–190, 1985.

Jeffrey H. Miller, "A Short Course in Bacterial Genetics: A Laboratory Manual and Handbook for *E. coli* and Related Bacteria", pp. 268–274., 1992.

Keehyun Han, et al., "Acetic Acid Formation in *Escherichia coli* Fermentation" *Biotechnology and Bioengineering*, vol. 39, pp. 663–671, 1992.

Gregory W. Luli, et al., "Comparison of Growth, Acetate Production, and Acetate Inhibition of *E. coli* Strains in Batch and Fed–Batch Fermentations", *Applied Environ. Microbio.*, vol. 56 pp, 1004–1011.

John Fieschko, et al., "Production of Human Alpha Consensus Interferon in Recombinant *Escherichia Coli*", *Chem. Eng. Commun.*, vol. 45, pp. 229–240, 1986.

Kunihiko Ohta, et al., "High Level Production of Human Proapo A–I by Fed–Batch Culture of Recombinant *Escherichia coli*", *Journal of Fermentation and Bioengineering*, vol. 75 pp. 155–157, 1993.

Xiao–Ming Yang, "Optimization of a cultivation process for recombinant protein production by *E. coli*", *Journal of Biotechnology*, vol. 23 pp. 271–289, 1992.

Peter Landwall, et al., "Removal of Inhibitors of Bacterial Growth by Dialysis Culture", *Journal of General Microbiology*, vol. 103 pp. 345–352, 1977.

Hans–Peter Meyer, et al., "Acetate formation in continuous culture of *E. coli* K12 D1 on defined and complex media", *Journal of Biotechnology*, vol. 1 pp. 355–358, 1984.

Heather L. MacDonald, et al., Effects of Medium Quality on the Expression of Human Interleukin–2 at High Cell Density in Fermentor Cultures of *E. coli* K–12, *Applied and Environ. Microbio*, vol. 56 pp. 640–645, 1990.

W. H. Holms, The Central Metabolic Pathways of *E. coli*: Relationship between Flux and Control at a Branch Point, Efficiency of Conversion to Biomass, and Excretion of Acetate, Curr. Topics Cell. Reg., vol. 28, pp. 69–105. (1986).

Keehyun Han, et al., "Relieving Effects of Glycine and Methione from Acetic Acid Inhibition in *E. coli* Fermentation", *Biotechnology and Bioengineering*, vol. 41, pp. 316–324, 1993.

(List continued on next page.)

*Primary Examiner*—Rebecca E. Prouty
*Assistant Examiner*—Lisa J. Hobbs
*Attorney, Agent, or Firm*—Foley & Lardner

[57] ABSTRACT

Disclosed herein is a new *E. coli* mutant, which is not capable of growing under anaerobic cultivation conditions, said mutant being capable of utilizing glucose as a carbon source but having a suppressed organic acid production under aerobic cultivation conditions. The mutant can advantageously be employed as an expression host system to produce recombinant proteins.

5 Claims, No Drawings

OTHER PUBLICATIONS

H.E. Reiling, et al., "Mass culture of *E. coli*: Medium development for low and high density cultivation of *E. coli* B/r in minimal and complex media", *Journal of Biotechnology*, vol. 2 pp. 191–206, 1985.

Marion M. Bradford, "A Rapid and Sensitive Method for the Quantitation of Microgram Quantities of Protein Utilizing the Principle of Protein–Dye Binding", *Analytical Biochem.*, vol. 72 pp. 248–254, 1976.

J.C. Diaz–Ricci, et al., "Effect of Alteration of the Acetic Acid Synthesis Pathway on the Fermentation Pattern of *E. coli*", *Biotechnology and Bioengineering*, vol. 38, pp. 1318–1324, 1991.

Baruch J. Davis, "Disc Electrophoresis—II: Method and Application to Human Serum Proteins". Ann. NY Acad. Sci. (1964).

E. COLI MUTANT WITH SUPPRESSED ORGANIC ACID PRODUCTION

This application is the National Stage Application of PCT/0186, filed Oct. 29, 1996, published as WO97/16530 May 9, 1997, which claims priority from application 1995-3, filed on Oct. 30, 1995 in the Republic of Korea.

BACKGROUND OF THE INVENTION

1. Field of the Invention

The present invention is related to a novel *E. coli* mutant strain with suppressed production of fermentative organic acids (especially acetate) during aerobic growth in glucose-supplemented medium. Reduction of the organic acids production of this mutant strain allows it to be a good host strain for recombinant protein production using high-cell-density aerobic fermentation.

2. Description of the Prior Arts

In order to produce useful recombinant proteins, *E. coli* is widely used as a host strain for high-cell-density aerobic fermentation. A substantial amount of glucose is added into the growth medium for the high-density growth of the host cells as well as for good expression of the recombinant gene, since it is an inexpensive and readily utilizable carbon and energy source. The major problem in the high-cell-density aerobic fermentation is production of fermentative acidic by-products of which acetate is the most predominant. Production of the acidic by-products, especially acetate, is a major factor in the limitation of high-cell-density growth and thereby the production of recombinant protein production (Han et al., Biotechnol. Bioeng., 39, 663 (1992); Luli et al., Appl. Environ. Microbiol., 56, 1004 (1990)).

In order to solve these problems, fed-batch culture technologies (Fieschko et al., Chem. Eng. Commun., 45, 2875 (1986); Ohta et al., J. Ferment. Bioeng., 75, 155 (1993); Yang, J. Biotechnol., 23, 271 (1992)), methods of removing organic acids produced from the culture (Landwall et al., J. Gen. Microbiol., 103, 345 (1977); Meyer et al., Proceedings of the 3rd European Congress on Biotechnology, (1984); MacDonald, Appl. Environ. Microbiol., 56, 640 (1990)), or changing media compositions (Holmes, Curr. Topics Cell. Regul. 28, 69 (1986); Han et al., Biotechnol. Bioeng., 41, 316 (1993); Reihng, J. Biotechnol. 2, 191 (1985); Mor et al., J. Ferment. Technol., 50, 519 (1972)) has been used. However, these methods also have limitations such that the slow growth rates and metabolically less active cultures resulting by these culture conditions often produce lower recombinant protein yields, that the control of complicated nutrient feeding is cumbersome and prone to errors (Chou et al., Biotechnol. Bioeng., 44, 952 (1994)), and that the salts added to the culture medium for pH control often cause inhibition of host growth and/or product production (Jensen et al., Biotechnol. Bioeng., 36, 1 (1990)).

For the glucose metabolism in *E. coli* strains under aerobic conditions, the carbon flow exceeding the capacity of TCA cycle, is converted to acetic acid which is excreted outside the cell (Majewski & Domach, Biotechnol. Bioeng., 35, 732 (1990)). The excreted acetic acid inhibits the growth of the host strain and the production of the desired recombinant protein. Acetate is formed from acetyl coenzyme A by the consecutive action of phosphotransacetylase (pia) and acetate kinase (ack). It was shown that mutational inactivation (by deletion of both pts and ack genes) of the acetate-forming enzymes produces a reduced, but still a significant amount of acetate. The mutation also caused lactate and pyruvate to accumulate(Diaz-Ricci et al., Biotechnol. Bioeng., 38, 1318 (1991)) to the level higher than its parental strain. These results suggest that there is an alternative pathway for acetate production and that inactivation of known acetate biosynthetic pathways redirects the carbon flow toward other organic acid.

Therefore, it had been needed a continued research to develop a new host strain deficient in production of organic acids overall and thereby increasing the yield of desired recombinant proteins.

SUMMARY OF THE INVENTION

Thus, an object of the present invention is to provide a new strain of *E. coli,* of which organic acid production is suppressed, thereby its growth or recombinant protein production is not inhibited.

The object can be accomplished by a new strain of *E. coli* JL1506 suppressing the production of organic acids during the growth on a glucose medium under an aerobic conditions.

Another object of the present invention is to provide a process for producing a recombinant protein which employs the strain of *E. coli* JL1506 as an expression host system.

The above and other objects, features and applications of the present invention will be apparent to those of ordinary skill in the aft from the following detailed explanation.

DETAILED EXPLANATION OF THE INVENTION

The new strain *E. coli* JL1506 may be obtained by the following procedure.

*E. coli* strain MG1655 (Guyer et al., Cold Spring Harbor Sym. Quant. Biol., 45, 135(1981) was provided with courtesy by *E. coli* Stock Center in Yale University, U.S.A., and was subjected to mutagenesis by ethyl methane sulfonate (EMS) by a standard method(Miller, Short course in bacterial genetics. Cold Spring harbor Laboratory(1992)), and mutants defective in pathways of producing organic acids under anaerobic conditions were screened. However, all of the screened mutants still produced organic acids to significant levels. It had been presumed that the mutants unable to grow under anaerobic conditions could not produce organic acids.

Therefore, the present inventors continued to screen mutants which could not grow under anaerobic conditions. One of the mutants screened is named as JL1031, which retains the growth rate of its parent strain, while its organic acid production from glucose is efficiently suppressed, under aerobic growth conditions. The mutation causing above phenotype was transferred into non-mutagenized parental strain MG1655 by P1 phage-mediated transduction and the resulting strain JL 1506 was confirmed to have the same phenotype as JL1031.

Such useful properties of the mutant strain of the present invention make it possible for the strain to be used as an expression host system for recombinant protein productions. The kind of the recombinant proteins which can be produced by using the strain *E. coli* JL1506 as an expression host system is not particularly limited. Nevertheless, it is more useful for the proteins whose expression is under the control of catabolite repression-sensitive promoters such as lac, tac, and the like. However, the host system according to the present invention still may be advantageously employed to produce other proteins, the expression of which is under the control of promoters which are not sensitive to the catabolite repression, when compared with the other host systems of other conventional strains of *E. coli.*

The transformation of E. coli JL1506 with a foreign gene coding for the recombinant protein can be carried out by following the methods well known, to those of ordinary skill in the art. The methods and conditions of the transformation, which do not restrict the present invention, can be determined by those of ordinary skill without difficulty depending on the kind of the recombinant protein, the size of the genes coding therefor, the selection marker, and the like.

The culture of the transformant E. coli JL1506 can be carried out in an appropriate culture medium under proper conditions, all of which can be determined by those of ordinary skill in the art.

The new mutant E. coli JL1506 according to the present invention can be obtained by treating the parent strain MG1655 with an appropriate mutagen and screening for mutants having the desired properties. As mutagens, chemical or UV light can be used. Gene manipulation also can be used to obtain the mutant of the present invention.

The mutation causing the above described phenotype of strain JL1506 was genetically mapped at 51–52 min. of E. coli chromosome.

A single mutation rendering the phenotype of normal growth aerobically but absence of growth anaerobically in glucose minimal media had not been reported previously, but for the first time has been found by the present inventors.

The present inventors named the mutational genotype as "glf-1031" (glucose fermentation defective) and indicated the mutant JL1031 having genotype glf-1031.

To avoid the presence of any possible mutation(s) on genes other than glf, the present inventors transduced the genotype of glf-1031 into MG 1655 by using P1 phage to give E. coli JL1506.

The present invention will be described in more detail through Examples in which Example 1 through 3 describes the isolation of E. coli JL1031 and construction of JL1506, and Examples 4 through 6 show the catabolite repression by glucose in the strains of JL1506 and MG1655.

Further, in order to examine the possibility of using the mutant E. coli JL 1506 as a host system for expressing genetically manipulated recombinant genes, strains JL1506/pMKT2-1 and MG1655/pMKT2-1 are obtained by transforming plasmid pMKT2-1 (Min et al., Korean Biochem. J., Nucleic Acid Res., 16, 5075(1988)) carrying native beta-galactosidase gene (lacZ) into JL 1506 and MG1655, respectively (Examples 7 and 8).

In Examples 9 and 10, a protein expression by using E. coli JL1506 as a host system is estimated by culturing the transformants of E. coli JL1506, MG1655, or C600, which carry plasmid pHIT1 (Huh et al., Korean Biochem. J., 23, 459(1990)) containing human lipocortin cDNA under the control of try promoter (Amann et al., Gene, 40, 183(1985)).

When beta-galactosidase or lipocortin is produced by the transformants, the protein yield was about two times higher in the strain JL 1506 than wild type controls of MG1655 or C600.

The various experiments carried out for the present invention are as follows:

1) Genetic experiments such as transduction, conjugation and gene mapping were carried out by following Miller's methods (Miller, A short: course in bacterial genetics, Cold Spring Harbor (1992)).

2) The activity of beta-galactosidase was measured by Min's method (Min et al., Nucleic Acid Res., 16, 5075 (1988)). Thus, a strain carrying gene coding for beta-galactosidase is cultured in LB medium containing 40 microgam/ml of ampicillin at 37° C. and 200 rpm for 12–16 hours. During the cultivation, 1 mM of IPTG (Isopropy-1-tliio-beta-D-galactopyranoside) was added to induce the expression of lacZ. Culture broth was sampled at a certain interval, and Z-buffer, chloroform, and 0.1% SDS were added thereto to disintegrate cells. The disintegrated cells were allowed to stand in 28° C. water bath for 5 minutes, 4 mg/ml of ONPG was added to stop the reaction. After centrifugation of the reaction mixture, the absorbance (420 nm) of the supernatant was measured by using a spectrophotometer (Pharmacia LKB-Ultraspec III).

3) The activity of beta-lactamase was measured by Iodine method(Han et al., Biotechnol., Bioeng., 39, 653(1992)). Thus, cells from the culture broth(5 ml) were suspended in a washing buffer(0.05M $Na_2HPO_4$, 0.05M $KH_2PO_4$, 0.014M NaCl, 0.01M $H_2SO_4$ in 0.1M phosphate buffered saline(PBS), 5 ml) and centrifuged. The precipitated cells were suspended in 0.1M PBS(5 ml) and disintegrated with Ultrasonic homogenizer US-150T for 5 minutes. Then, the resulting was centrifuged at 4° C. and 15000 rpm to give a cell homogenate.

To a test tube(A), 20 mM benzyl penicillin(0.25 ml), 0.1M PBS(1.25 ml) and cell homogenate(0.5 ml) were added, and the mixture was reacted at 30° C. for 20 minutes. To a control test tube(B), 0.1M PBS(2 ml) was placed. Iodine(2.5 ml) was added to the test tubes, and they were allowed to stand for 10 minutes and measured for their absorbance at 490 nm.

4) Lipocortin was identified by SDS-polyacrylamide gel electrophoresis as a band at 37 kD(Davis, Ann. Rev. NY Acad. Sci., 121, 404(1964)). Image densitometer (Bio-Rad GS-670) was employed for quantification.

4-1) Quantification of lipocortin produced by cell: The culture broth after the aerobic cultivation for 12 hours was inoculated in LB medium(20 ml) containing 1% glucose to a concentration of 2% so that the absorbance at 600 nm can be 0. 1, and cultivated for 10 hours. The culture broth (1 ml) was mixed with 0.5 ml of SDS solution(distilled water, 4.0 ml, 0.5M Tris-Cl, 1.0 ml; glycerol, 0.8 ml; SDS, 10%; β-mercaptoethanol, 0.4 ml; 0.1% bromophenol blue, pH 6.8), and heat-treated at 95° C. for 5 minutes. Twenty microliters of the reaction mixtures were taken and subjected to an electrophoresis on 10% SDS-polyacrylamide gel(SDS-PAGE).

4-2) Quantification of lipocortin among soluble proteins: Cultivation was carried out by following the same procedure in the above 4-1), and the culture broth(3 ml) was taken at 6 hours and 10 hours and centrifuged to collect cells. Cels were suspended in Tris buffer(1 ml) containing 5 mM EDTA, and disintegrated with an ultrasonic homogenizer. The supernatant were employed as soluble protein fractions. To 20 microliters of supernatant, the equal amount of SDS was added, and the resulting mixture was treated by the same procedure as that of 4-1). Lipocortin was quantified by 12% SDS-PAGE.

For the present invention, the new mutant E. coli JL 1506,which cannot utilize glucose under anaerobic conditions, and the organic acid production of which is suppressed, when cultured at a high cell concentration under aerobic conditions, is provided. The mutant can be effectively utilized as a useful host system to produce recombinant protein. Further it can be used to develop new mutants by blocking genes involved in the organic acid production.

PREFERRED EMBODIMENTS OF THE INVENTION

The present invention will be embodied by way of the following examples. However, these examples are provided for the illustration purpose only and should not be constrained as limiting the scope of the invention, which is properly delineated in the accompanying claims. The parts or percents in the Examples are based on the weight, unless indicated otherwise.

EXAMPLE 1

*E.coli* wild type strain MG1655 was treated with EMS. The mutagenized cells were plated on Luria-Bertani (LB: trypton, 10 g; yeast extract, 5 g; NaCl, 5 g; distilled water 1 liter) agar plate and incubated at 37° C. for single colonies. The colonies were replica plated on two sets of glucose (final con. 1%)-supplemented M56 minimal medium ($KH_2PO_4$, 10.6 g; $Na_2HPO_4$, 17.4 g; 10% $MgSO_4 \cdot 7H_2O$, 4 ml; 1% $(NH_4)_2SO_4$, 2 ml; 0.05% $FeSO_4 \cdot 7H2O$, 2 ml; distilled water 1 liter, pH 7.0) agar plates. One set was incubated aerobically and the other set was incubated anaerobically in an anaerobic jar (BBL) at 37° C. A mutant stain, *E. coli* JL1031, was identified as a colony which grew normally aerobically but did not grow anaerobically even after 48 hr.

EXAMPLE 2

In order to place a positive marker in the vicinity of the mutation (tentatively named as glf-1031, see Example 4 for more explanation) causing the deficiency of the anaerobic growth in JL1031 (Glf, for further characterization of the mutant), transposon Tn10 was inserted near the glf-1031. For this purpose MG1655 (Glf⁺) was infected with lambda NK561 Foster, Cell, 23, 215(1981)) and plated on LB/Tet (15 µg/ml). The resulting etracycline-resistant(Tc-r) colony pools were used for propagation of phage P1vir. Stain JL1031 was infected with the P1 lysate and plated on LB/Tet plate for Tc-r transductants. The transductants were replica plated on glucose minimal medium and a colony able to grow on the medium anaerobically (Glf⁺) was obtained. P1 lysate prepared on the Glf transductant were used to transduce JL 1031(Glf⁺) to Tc-r. Among 61 Tc-r transductants tested, 16 were unable to grow anaerobically on the glucose minimal medium. These results show that the transposon Tn10 O (zzz-1051::Tn10) was placed nearby the glf-1031, and that these are 26.2% (16/61) co-transducible. One of the resulting 45 Glf zzz-1031::Tn10 transductants was chosen and named as JL1501 (glf-1031, zzz-1051::Tn10).

EXAMPLE 3

The glf-1031 mutation was re-transduced into MG1655 using JL1501 as donor, and one of resulting Glf zzz-1051::Tn10 transductants was randomly picked, was named as JL1506 (glf-1031, zzz-1051::Tn10), and used for filter characterization described as below. The *E. coli* strain JL1506 was deposited under the Budapest Treaty on Oct. 19, 1995 at Korean Collection for Type Cultures located at GERI Korea Institute of Science and Technology, PO Box 115, Yusong, Taejon, Republic of Korea and given an accession number KCTC 0204BP.

Hfr-conjugation and P1-transduction analysis revealed that the zzz-1051::Tn10 is co-transducible with nupC-3146::Tn10 located at 51.75 min. of the *E. coli* chromosome. The reversion frequency of the glf-1031, determined by frequency of the reversion on the glucose minimal medium under anaerobic condition, was found to be $8 \times 10^{-3}$.

EXAMPLE 4

Strain JL1506 and its parental stain MG1655 were tested for their ability to grow on M56 medium supplemented with various carbon sources supplemented at a final concentration of 1%, under both aerobic and anaerobic growth conditions. For this test, these strains were patched on LB plate and incubated aerobically at 37° C. overnight. The overnight grown cultures were replica plated on duplicates of appropriate sugar minimal medium plates. One copy of the replica plate was incubated aerobically and the second copy was incubated in anaerobic jar (BBL). Growth was scored after 18 hr for aerobic cultures or after 48 hr for anaerobic cultures. The ability of these strains to utilize various carbon sources under aerobic and anaerobic growth conditions were summarized in Table 1.

TABLE 1

| strain | Growth | | | | | | | |
|---|---|---|---|---|---|---|---|---|
| carbon | Aerobic | | | | Anaerobic | | | |
| source | glu | fru | gly | gly/NO₃ | glu | fru | gly | gly/NO₃ |
| JL1506 | + | + | + | + | − | + | − | + |
| MG1655 | + | + | + | + | + | + | − | + |

The mutant strain JL1506 was unable to grow on glucose anaerobically, while its parental strain MG1655 grew normally under the same condition. However the mutant grew normally in glycerol/$NO_3^-$ (20 mM) minimal medium anaerobically. These results suggest that the JL1506 mutant is not defective in the anaerobic respiration pathway but may be defective in glucose fermentation pathway. For these reasons, the mutational locus in JL1506 was tentatively designated as glf (glucose fermentation defective).

EXAMPLE 5

Mutant strain JL 1506 and its control strain MG 1655 were compared for their ability to produce organic acids during aerobic growth in glucose medium. Aerobically overnight grown LB culture of each strain was inoculated in 250 ml flask containing 50 ml of M56/glucose (final con. of 0.5%) medium to a initial O.D. of 0.01 at 600 nm. The cultures were incubated in rotary shaker at 37° C., 200 rpm. Aliquots of the cultures were collected at every 3 hr. Absorbance at 600 ml for growth and concentrations of organic acids were determined for acid production using HPLC. For organic acids analysis, 1 ml of the culture sample centrifuged at room temperature. Supernatant were centrifuged again after mixing with equal volume of 5 mM $H_2SO_4$. The resulting supernatant were filtered through membrane filter (Gelman, 0.2 µm) and store at −20° C. until analysis. 10 µl of the filtrate was subjected HPLC (Spectra Physics Co.) analysis using Aminex HPX-87H column (300×7.8 mm; Bio-Rad) for quantification of organic acids. As an eluent 0.01M $H_2SO_4$ was employed at a flow rate of 0.4 ml/min. An UV detector at 210 nm was used.

As results, compared with maximum concentrations of each organic acid produced by each culture, JL1506 produced 0.3 mM of acetic acid, 0.8 mM of formic acid, and 0.3 mM lactic acid, while the MG1655 produced 20.6 nM of acetic acid, 14.9 mM of formic acid and 0.4 mM of lactic acid. Thus, for the inventive mutant JL1506, its organic acid production is significantly suppressed. Especially, it produced acetic acid only 1% level of its wild type control.

EXAMPLE 6

The effect of glucose on the growth of JL1506 and MG1655 were compared to monitoring growth in LB with various glucose concentrations. Aerobically overnight grown LB culture of each strain was inoculated in 125 ml flask containing 10 ml of LB supplemented with glucose at a 0.2%, 0.5%, or 1% final concentration. Cultures were incubated in a rotary shaker at 37° C., 200 rpm. The absorbance at 600 nm of the culture broth was measured for every hour to determine the growth of the strains. The results are shown in Table 2.

TABLE 2

| Strain | O.D. at 600 nm | | | |
|---|---|---|---|---|
| Time/Glc con | JL1506 | | | MG1655 |
| (%) | 0.2% | 0.5% | 1.0% | 1.0% |
| 0 | 0.03 | 0.05 | 0.02 | 0.15 |
| 4 | 3.05 | 2.5 | 2.96 | 2.51 |
| 8 | 6.15 | 7.1 | 6.87 | 4.04 |
| 10 | 6.22 | 6.81 | 7.13 | 4.03 |
| 12 | 6.2 | 6.5 | 7.18 | 3.84 |

As can be seen from Table 2, the strain JL1506 showed an increase of the growth as the concentration of glucose increase, while the strain MG1655 showed a decrease of the growth from 8 hours of the cultivation due to the accumulation of the organic acids produced by itself.

Further, the maximum growth of JL1506 reached to an absorbance of 7.18, which is almost twice that (4.04) of the parent strain.

EXAMPLE 7

To test feasibility of the strain JL1506 to be developed as a recombinant protein expression host, productivity of plasmid encoded proteins were tested in JL1506 and MG1655. Plasmid pNMT2-1 (Min et al., Nucleic Acid Res., 16, 5075 (1988)), which encodes beta-galactosidase (lacZ) and beta-lactamase gene (bla) was introduced to JL1506 and MG1655. The resulting transformant, JL1506/pMKT2-1 or MG1655/pMK2-1 was cultured in 250 ml flask containing 10 ml of LB/glucose (0.5%) at 37° C., 200 rpm. Absorbance at 600 nm for cell growth, enzyme activities of beta-galactosidase and beta-lactamase, and plasmid stability were determined.

As results, it was confirmed that JL 1506/pMKT2-1 which is derived from JL1506 of the present invention retained the plasmid stably enough that 100% of the plasmid were maintained after sub-culture of 18 generations.

The profiles of growth and enzyme activities are shown in Table 3.

TABLE 3

| | Volumetric Enzyme Activity(units/ml) | | | | | |
|---|---|---|---|---|---|---|
| Strain | JL1506/pMKT2-1 | | | MG1655/pMKT2-1 | | |
| Time | O.D. | β-gal* | β-lac | O.D. | β-gal* | β-lac |
| 0 | 0.38 | 0.34 | 0.04 | 0.3 | 1.4 | 0.03 |
| 4 | 8.34 | 155.42 | 5.18 | 4.62 | 25.22 | 5.07 |
| 8 | 7.23 | 148.71 | 10.97 | 4.55 | 28.49 | 6.2 |
| 10 | 8.32 | 151.71 | 11.97 | 4.62 | 18.71 | 7.18 |
| 12 | 7.95 | 242.86 | 13.13 | 4.69 | 21.1 | 7.89 |

*: × $10^3$ units

The final O.D. (12 hr) of JL1506/pMKT2-1 culture was 7.95, while that of the MG1655/pMKT2-1 was 4.69. JL1506/pMKT2-1 produced about 70% more cell yield judged upon the O.D. values than its wild type control, MG1655/pMKT2-1. For the production of beta-galactosidase, the mutant of the present invention produced 11.5 times higher total (volumetric) activity than its wild type control. Therefore, the mutant produced about 6.8 times more specific activity (activity units/O.D.) than its control. For beta-lactamase encoded in the same plasmid of pMKT2-1, the mutant produced 66% more total activity than its control. However, no difference was observed in specific activities between the mutant and wild type control.

These results shows that JL1506 of the present invention is very useful to be developed as a host strain for recombinant protein productions from plasmid encoded genes.

EXAMPLE 8

In order to determine the extent of catabolite repression on the expression of a plasmid encoded gene (beta-galactosidase) in JL1506 of the present invention during the growth in glucose medium, its beta-galactosidase activities and cell growth were determined in LB/glucose cultures with or without cAMP supplement. Strain MG1655 was grown under the same conditions for comparison. These strains were inoculated in 250 ml flask containing 20 ml of LB/glucose (0.1%) with or without addition of cAMP (final con. of 5 nM). The cultures were incubated in a rotary shaker at 37° C., 200 rpm. Growth and beta-galactosidase activity were determined. The results are shown in Table 4.

TABLE 4

| Strain | JL1506/pMKT2-1 | | | | MG1655/pMKT2-1 | | | |
|---|---|---|---|---|---|---|---|---|
| Time | −cAMP | | +cAMP | | −cAMP | | +cAMP | |
| (h) | OD | β-gal | OD | β-gal | OD | β-gal | OD | β-gal |
| 0 | 0 | 0.12 | 0.02 | 0.1 | 0.1 | 0.09 | 0.05 | 0.08 |
| 4 | 1.8 | 30.5 | 1.42 | 26.2 | 2.5 | 12.7 | 2.02 | 35.52 |
| 8 | 3.9 | 55.1 | 3.02 | 52.1 | 3.1 | 11.8 | 2.93 | 35.00 |
| 10 | 4.8 | 43.7 | 3.67 | 57.6 | 3.3 | 5.45 | 3.14 | 24.76 |
| 12 | 5.7 | 45.8 | 4.46 | 66.2 | 3.5 | 4.04 | 3.25 | 19.41 |

Wild type strain MG 1655 showed severe repression on the beta-galactosidase expression in the absence of cAMP and the repression effect was pronounced as cell get older. Addition of cAMP relieved the catabolite repression effect by glucose. However, the mutant strain JL1506 of the present invention did not show the catabolite repression effect and the enzyme activities were much higher than those of MG1655 with cAMP. These results demonstrate that the inventive mutant strain JL 1506 has very little catabolite repression by glucose in the medium on the expression of the plasmid encoded gene.

EXAMPLE 9

Productivities of a heterologous recombinant protein in flask batch cultures of JL1506 and two control strains, MG1655 and C600 were determined and compared. Plasmid pHT1 (Huh et al., Korean Biochem. J., 23, 459 (1990) containing human lipocortin cDNA was introduced by transformation into the inventive JL1506, its wild type parental strain MG1655, and C600 the host strain reported to overproduce the lipocortin protein in the above report. Each of these transformants (JL 1506/pHT1, MG1655/pHT1, and C600/pHT1) was inoculated in 250 ml flask containing 20 ml of LB/glucose (final con. of 0.1%) medium and incubated in a rotary shaker at 37° C., 200 rpm. At appropriate culture times, the culture broths were collected and determined absorbance at 600 nm for growth. The culture samples were also analyzed for the amount of total lipocortin produced in the total cellular protein. For the lipocortin analysis, 1 ml of culture broth was mixed with 0.5 ml of SDS sample buffer (0.5M Tri-HCl (pH 6.8), 1.0 ml; 10%(w/v) glycerol, 0.8 ml; 10% (w/v) SDS; beta-mercaptoethanol, 0.4 ml; Bromophenol blue, 0.1% (w/v); distilled water, 4.0 ml) and heat treated at 95° C. for 5 min. 20 μl of the samples were subjected to 10% SDS-PAGE. After electrophoresis, the gel was stained with Coomassie Brilliant Blue and scanned with Image Densitometer (Bio-Rad Model GS-670). The lipocortin band was identified by its reported molecular weight (37 kd) and its relative band volume (density×band area) was compared in Table 5.

TABLE 5

| Time | JL1506/pHT1 | | MG1655/pHT1 | | C600/pHT1 | |
|---|---|---|---|---|---|---|
| | Absorb. | Lipocortin | Absorb. | Lipocortin | Absorb. | Lipocortin |
| 0(h) | 0.09 | | 0.11 | | 0.09 | |
| 4 | 4.81 | 6.13 | 3.65 | 0.94 | 5.70 | 3.44 |
| 8 | 6.53 | | 4.07 | | 6.41 | |
| 10 | 6.98 | 9.93 | 4.06 | 1.00 | 6.50 | 4.64 |
| 12 | 7.38 | | 4.03 | | 6.64 | |

The mutant JL 1506 of the present invention showed the highest cell yield among the strains tested in this aerobic LB/glucose batch cultures. It also produced the highest lZpocortin productivity among all the strains tested. The 10 hr sample of JL1506/pHT1 produced lipocortin 9.93 times higher than that of MG 1655/pHT1 (10 hr). The amount of lipocortin produced by the inventive mutant was almost twice of that produced in C600/pHT1.

EXAMPLE 10

The amounts of soluble lipocortin produced in equal amount of soluble cell fractions of JL1506 and two other control strains were determined and compared. The culture conditions and strains used were same as described in Example 9. Culture broth 3 ml were collected at 6 hr and 10 hr culture times and centrifuged at room temperature to harvest the cells. The resulting cell pellet was resuspended in 1 ml of Tris-HCl buffer with EDTA (final conc. of 5 mM). Soluble cellular protein fractions were prepared by disintegrating the cells with Ultrasonic Homogenizer and taking supernatant after centrifugation at 4° C. The protein concentrations in the soluble cellular protein fractions were determined by Bradford method (Bradford, Anal. Biochem., 72, 248 (1976). The resulting supernatant was mixed with volume of the SDS sample buffer and equal amount of soluble protein were subjected to 10% SDS-PAGE and relative productivity of the lipocortin protein was determined as describe in Example 9. The results are shown in Table 6.

TABLE 6

Relative amount of lipocortin production in equal amount of soluble cellular protein fractions.

| | Relative lipocortin productivity in soluble fraction* | | |
|---|---|---|---|
| Lipocortin | JL1506/pHT1 | MG1655/pHT1 | C600/pHT1 |
| Soluble after 6 h | 4.32 | 0.89 | 1.64 |
| Soluble after 10 h | 4.64 | 1.00 | 0.89 |

*: Relative lipocortin productivity in soluble fraction. The lipocortin band volume(density × band area) of MG1655/pHT1 at 10 hr was considered as 1.0 for comparison purpose.

Based upon the productivity of soluble lipocortin produced in unit amount of soluble cell proteins (specific productivity), the strain JL 1506/pHT1 also showed the highest productivity of soluble lipocortn among the strains tested. It produced lipocortin 4.64 times higher than that of MG1655/pHT1. C600/pHT1 produced more soluble lipocortin at 6 hr than at 10 hr. JL1506/pHT1 produced 2.83 times (4.64/1.64) higher productivity than 6 hr culture of C600/pHT1. These results demonstrate that the inventive strain JL1506 perform superbly as a host strain for the lipocortin production.

We claim:

1. An *E. coli* mutant which is not capable of growing under anaerobic culture conditions with glucose as a carbon source, said mutant being capable of utilizing glucose as a carbon source under aerobic growth conditions but having organic acid production under aerobic growth conditions which is suppressed compared to its parent strain.

2. The *E. coli* mutant of claim 1, which is *E. coli* JL1506 deposited according to Budapest Treaty under an accession number of KCTC 0204BP.

3. A process for producing a recombinant protein utilizing an *E. coil* strain as a expression host system, said process comprising (a) introducing a foreign gene coding for a desired recombinant protein into an *E. coli* mutant according to claim 1 to obtain a transformant *E. coli* mutant carrying said foreign gene;

(b) cultivating the transformant *E. coli* mutant obtained in step (a) under in appropriate culture medium to produce the desired protein; and (c) recovering the desired protein from culture broth.

4. The process of claim 3, wherein said *E. coli* mutant *E. coli* JL1506 deposited according to Budapest Treaty under an accession number of KCTC 0204BP.

5. The process of claim 3, wherein said protein is lipocortin.

* * * * *